United States Patent
Diefenbacher et al.

(10) Patent No.: US 8,197,645 B2
(45) Date of Patent: Jun. 12, 2012

(54) PROCESS FOR SEPARATING PROPYLENE GLYCOL FROM AQUEOUS COMPOSITIONS

(75) Inventors: Armin Diefenbacher, Freisbach (DE); Hans-Georg Goebbel, Kallstadt (DE); Stefan Bitterlich, Dirmstein (DE); Hartwig Voss, Frankenthal (DE); Henning Schultz, Mannheim (DE); Anna Forlin, Vigonza (IT); Renate Patrascu, Stade (DE)

(73) Assignees: BASF Aktiengesellschaft, Ludwigshafen (DE); The Dow Chemical Company, Midland, MI (US)

( * ) Notice: Subject to any disclaimer, the term of this patent is extended or adjusted under 35 U.S.C. 154(b) by 905 days.

(21) Appl. No.: 12/159,321

(22) PCT Filed: Dec. 13, 2006

(86) PCT No.: PCT/EP2006/069647
§ 371 (c)(1),
(2), (4) Date: Jun. 26, 2008

(87) PCT Pub. No.: WO2007/074066
PCT Pub. Date: Jul. 5, 2007

(65) Prior Publication Data
US 2008/0289948 A1  Nov. 27, 2008

Related U.S. Application Data

(60) Provisional application No. 60/775,789, filed on Feb. 23, 2006.

(30) Foreign Application Priority Data

Dec. 29, 2005 (IT) .............................. MI2005A2524

(51) Int. Cl.
*B01D 1/26* (2006.01)
*B01D 3/14* (2006.01)
*C07C 29/80* (2006.01)
*C07C 31/18* (2006.01)

(52) U.S. Cl. ..... 203/2; 159/17.1; 159/47.1; 159/DIG. 8; 203/18; 203/80; 203/DIG. 16; 210/652; 210/664; 549/531; 568/868; 568/872

(58) Field of Classification Search ................. 159/17.1, 159/47.1, DIG. 8; 203/2, 18, 80, DIG. 16; 210/652, 664; 549/531; 568/868, 872
See application file for complete search history.

(56) References Cited

U.S. PATENT DOCUMENTS

| 4,511,437 A * | 4/1985 | Heck et al. ...................... 203/19 |
| 5,425,853 A | 6/1995 | Berg |
| 5,552,023 A * | 9/1996 | Zhou ............................... 203/18 |
| 6,417,411 B2 * | 7/2002 | Kakimoto et al. ............. 568/867 |
| 6,514,388 B1 * | 2/2003 | Adrian et al. ................... 203/18 |
| 6,605,192 B1 * | 8/2003 | Theis et al. ....................... 203/3 |
| 7,141,683 B2 * | 11/2006 | Haas et al. ..................... 549/531 |
| 2002/0010378 A1 | 1/2002 | Kakimoto et al. |
| 2006/0161010 A1 * | 7/2006 | Gobbel et al. ................. 549/531 |
| 2007/0238888 A1 * | 10/2007 | Goebbel et al. ............... 549/541 |

FOREIGN PATENT DOCUMENTS

| EP | 0 523 990 A1 | 1/1993 |
| FR | 2 301 288 | 9/1976 |
| WO | WO 2004/009571 A1 | 1/2004 |

* cited by examiner

*Primary Examiner* — Virginia Manoharan
(74) *Attorney, Agent, or Firm* — Oblon, Spivak, McClelland, Maier & Neustadt, L.L.P.

(57) ABSTRACT

The present invention relates to a process for separating at least one propylene glycol from a mixture (M) comprising water and said propylene glycol, said process comprising (I) evaporating the mixture in at least two evaporation and/or distillation stages at decreasing operating pressures of the evaporators and/or distillation columns obtaining mixture (M') and mixture (M"); (II) separating the mixture (M') obtained in (I) in at least one further distillation step, obtaining a mixture (M-I) comprising at least 70 wt.-% of water and a mixture (M-II) comprising less than 30 wt.-% of water.

12 Claims, No Drawings

US 8,197,645 B2

PROCESS FOR SEPARATING PROPYLENE GLYCOL FROM AQUEOUS COMPOSITIONS

BACKGROUND OF THE INVENTION

Among publications on the subject of the preparation of propylene oxide, there are only a few which are concerned with the treatment of the waste water and recovering byproducts from the reaction mixture.

WO 2004/000773 refers to a process of separating 1-methoxy-2-propanol and 2-methoxy-1-propanol from aqueous compositions, comprising: dewatering of the aqueous composition comprising 1-methoxy-2-propanol and 2-methoxy-1-propanol to a concentration of 1-methoxy-2-propanol and 2-methoxy-1-propanol of at least 90 percent by weight in total and isolation of 1-methoxy-2-propanol, 2-methoxy-1-propanol or mixtures thereof by means of distillation. According to WO 2004/000773, dewatering of the aqueous composition can be achieved by a membrane separation. Thereby the aqueous composition comprising 2-methoxy-1-propanol and 1-methoxy-2-propanol is contacted with a semipermeable, hydrophilic membrane in a suitable apparatus either in liquid phase as pervaporation step or in the gaseous phase as vapor permeation step. Across the semipermeable membrane a pressure difference is established. The permeate will substantially contain water and only a minor amount of 1-methoxy-2-propanol and 2-methoxy-1-propanol. According to WO 2004/000773, the major amount of 1-methoxy-2-propanol and 2-methoxy-1-propanol fed to the apparatus will not pass the membrane and can be collected as a retentate with a reduced water content.

U.S. Pat. No. 5,599,955 provides an integrated process for the production of propylene oxide from an alternate feedstream such as synthesis gas. In the process, propylene oxide is produced from a feedstream comprising hydrogen and a carbon oxide. The propylene stream is epoxidized with hydrogen peroxide which has been produced from hydrogen separated from a portion of the feedstream. The spent water stream produced by the epoxidation reaction is treated to remove heavy components and returned to the hydrogen peroxide production zone. The recycling of spent water from the epoxidation reaction zone and the removal of heavy compounds eliminates a low value water stream and the recovery of heavy hydrocarbons therefrom produces a valuable secondary product. The spent water stream is passed to a separation zone such as an evaporator, a distillation zone or a sorption zone.

US 2002/010378 discloses a composite process for subjecting ethylene to catalytic gas phase oxidation thereby obtaining ethylene oxide and causing this ethylene oxide to react with water thereby obtaining ethylene glycol. In the production of ethylene glycol by the supply of the aqueous ethylene glycol solution to a concentrating treatment at the multi-effect evaporator, the method contemplated by US 2002/010378 for the production of ethylene glycol comprises utilizing as the source of heating at least one specific step the steam generated in the multi-effect evaporator.

U.S. Pat. No. 6,288,287 discloses a process for preparing a glycerol from a crude glycerol comprising a glycerol, a diol and water, comprising feeding the crude glycerol to a preparation apparatus comprising two or more, serially connected flash towers and a distillation tower connected to a final flash tower, wherein a bottom fraction of each flash tower is fed to a subsequent flash tower. According to U.S. Pat. No. 6,288,287, there is provided a process for preparing a glycerol from a crude glycerol comprising a glycerol, a diol and water, comprising the steps of: feeding the crude glycerol to a preparation apparatus comprising two or more, serially connected flash towers and a distillation tower connected to a final flash tower, wherein a bottom fraction of each flash tower is fed to a subsequent flash tower.

U.S. Pat. No. 5,269,933 and EP 0 532 905 A disclose a method for separation of a mixture of an organic fluid and water, such as carboxylic acids, including, for example, acetic acid, propionic acid, aromatic amines, including, for example, aniline, phenol, and glycerin. The method is a combination of a distillation, a water-selective pervaporation and a reverse osmosis and is particularly suitable for the separation of glycol and water. The process according to U.S. Pat. No. 5,269,933 comprises distilling the mixture, performing a water-selective pervaporation to bottom product obtained from the distillation step to obtain a residue and permeate, applying a reverse osmosis to at least the distillate to obtain a residue and permeate, and feeding the residue obtained from the reverse osmosis for performing thereon the distillation step, such that segregated organic fluid is present as residue from the water-selective pervaporation, and segregated water is present as the permeate from the water-selective pervaporation step as well as the permeate from the reverse osmosis step.

According to EP 0 324 915 A, valuable materials can be separated from aqueous solutions by extraction and/or distillation; the solution can be previously concentrated by reverse osmosis. The valuable materials are separated solely by distillation following concentration of the solution by optionally multi-stage reverse osmosis. According to the process disclosed in EP 0 324 915 A, the valuable material leaves the distillation column with the bottom stream or the top stream.

U.S. Pat. No. 6,712,882 discloses a process for treating waste water from an industrial process for producing propylene oxide, which process involves the steps of: (a) subjecting the waste water to a multi-effect evaporation treatment resulting in a vaporous top fraction and a liquid bottom fraction containing the non-volatile contaminants; and (b) condensing at least part of the vaporous top fraction into a liquid stream which is subject to a stripping treatment resulting in an overhead stream containing volatile waste organic material and purified water as the liquid bottom stream.

Accordingly, the prior art describes several options for treating waste water comprising organic compounds.

It is an object of the present invention to provide a process for recovering propylene glycol from a mixture comprising propylene glycol and water.

It is yet another object of the present invention to provide a process for recovering propylene glycol from a mixture comprising propylene glycol and water with improved yield and improved long term performance.

It is yet another object of the present invention to provide a process for recovering propylene glycol from a mixture comprising propylene glycol and water, wherein this mixture is obtained as a by-product from an epoxidation process where propene is oxidized to obtain propylene oxide.

SUMMARY OF THE INVENTION

Therefore, the present invention provides a process for separating at least one propylene glycol from a mixture (M) comprising water and said propylene glycol, said process comprising (I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water.

The present invention also relates to a process for separating at least one propylene glycol from a mixture (M) comprising water and said propylene glycol, said process comprising (I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water, wherein mixture (M") is further separated into mixture (M-Ia) comprising at least 90 wt.-10% of water and mixture (M-Ib) comprising less than 95 wt.-% of water by means of reverse osmosis.

The present invention also relates to a process for separating at least one propylene glycol from a mixture (M) comprising water and said propylene glycol, said process comprising (I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water;

(III) separating the at least one propylene glycol from the mixture (M-II) in at least one further distillation step.

The present invention also relates to a process for separating at least one propylene glycol from a mixture (M) comprising water and said propylene glycol, said process comprising (I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water, wherein mixture (M-I) is further separated into mixture (M-Ia) comprising at least 90 wt.-% of water and mixture (M-Ib) comprising less than 95 wt.-% of water by means of reverse osmosis.

The present invention also relates to a process for separating at least one propylene glycol from a mixture (M) comprising water and said propylene glycol, said process comprising (I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water, wherein mixture (M") and mixture (M-I) are combined and further separated into mixture (M-Ia) comprising at least 90 wt.-% of water and mixture (M-Ib) comprising less than 95 wt.-% of water by means of reverse osmosis.

The present invention also relates to a process for separating at least one propylene glycol from a mixture (M) comprising water and said propylene glycol, said process comprising (I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water;

(III) separating the at least one propylene glycol from the mixture (M-II) in at least one further distillation step, wherein mixture (M-I) is further separated into mixture (M-Ia) comprising at least 90 wt.-% of water and mixture (M-Ib) comprising less than 95 wt.-% of water by means of reverse osmosis.

The present invention also relates to a process for separating at least one propylene glycol from a mixture (M) comprising water and said propylene glycol, said process comprising (I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water, wherein the mixture (M) is obtained as a by-product in a process for the epoxidation of propylene comprising the step (a) reacting propylene with a hydroperoxide in the presence of at least one solvent and at least one catalyst to obtain a mixture (M-a) comprising propylene oxide.

The present invention also relates to a process for separating at least one propylene glycol from a mixture (M) comprising water and said propylene glycol, said process comprising (I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water, wherein in step (I) three evaporation stages (E1) to (E3) are carried out at decreasing operating pressures in the ranges (E1) 1.5 to 5.5 bar at a temperature of 111 to 155° C.,
(E2) 1.3 to 5.0 bar at a temperature of 107 to 152° C.,
(E3) 0.7 to 4.0 bar at a temperature of 90 to 144° C.

The present invention also relates to a process for separating at least one propylene glycol from a mixture (M) comprising water and said propylene glycol, said process comprising (I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water;

(III) separating the at least one propylene glycol from the mixture (M-II) in at least one further distillation step;

wherein in step (I) three evaporation stages (E1) to (E3) are carried out at decreasing operating pressures in the ranges
(E1) 1.5 to 5.5 bar at a temperature of 111 to 155° C.,
(E2) 1.3 to 5.0 bar at a temperature of 107 to 152° C.,
(E3) 0.7 to 4.0 bar at a temperature of 90 to 144° C.

The present invention also relates to a process for separating at least one propylene glycol from a mixture (M) comprising water and said propylene glycol, said process comprising
  (I) evaporating the mixture in at least two evaporation and/or distillation stages at decreasing operating pressures of the evaporators and/or distillation columns obtaining mixture (M') and mixture (M");
  (II) separating the mixture (M') obtained in (I) in at least one further distillation step, obtaining a mixture (M-I) comprising at least 70 wt.-% of water and a mixture (M-II) comprising less than 30 wt.-% of water;
  (III) separating the at least one propylene glycol from the mixture (M-II) in at least one further distillation step,
wherein mixture (M-I) is further separated into mixture (M-Ia) comprising at least 90 wt.-% of water and mixture (M-Ib) comprising less than 95 wt.-% of water by means of reverse osmosis, and
wherein in step (I) three evaporation stages (E1) to (E3) are carried out at decreasing operating pressures in the ranges
(E1) 1.5 to 5.5 bar at a temperature of 111 to 155° C.,
(E2) 1.3 to 5.0 bar at a temperature of 107 to 152° C.,
(E3) 0.7 to 4.0 bar at a temperature of 90 to 144° C.

The present invention also relates to a process for separating at least one propylene glycol from a mixture (M) comprising water and said propylene glycol, said process comprising
  (I) evaporating the mixture in at least two evaporation and/or distillation stages at decreasing operating pressures of the evaporators and/or distillation columns obtaining mixture (M') and mixture (M");
  (II) separating the mixture (M') obtained in (I) in at least one further distillation step, obtaining a mixture (M-I) comprising at least 70 wt.-% of water and a mixture (M-II) comprising less than 30 wt.-% of water;
wherein mixture (M-I) is further separated into mixture (M-Ia) comprising at least 90 wt.-% of water and mixture (M-Ib) comprising less than 95 wt.-% of water by means of reverse osmosis;
wherein the mixture (M) is obtained as a by-product in a process for the epoxidation of propylene comprising the step
  (a) reacting propylene with a hydroperoxide in the presence of at least one solvent and at least one catalyst to obtain a mixture (M-a) comprising propylene oxide; and
wherein in step (I) three evaporation stages (E1) to (E3) are carried out at decreasing operating pressures in the ranges
(E1) 1.5 to 5.5 bar at a temperature of 111 to 155° C.,
(E2) 1.3 to 5.0 bar at a temperature of 107 to 152° C.,
(E3) 0.7 to 4.0 bar at a temperature of 90 to 144° C.

DETAILED DESCRIPTION OF THE INVENTION

According to the present invention, the process for separating at least one propylene glycol from a mixture (M) comprising water and said propylene glycol comprises two steps. In a first step (I), a mixture (M') is obtained, which is then subjected to a second step (II). According to the present invention, the process for separating at least one propylene glycol from a mixture (M) comprising water and said propylene glycol comprises
  (I) evaporating the mixture in at least two evaporation and/or distillation stages at decreasing operating pressures of the evaporators and/or distillation columns obtaining mixture (M') and mixture (M");
  (II) separating the mixture (M') obtained in (I) in at least one further distillation step, obtaining a mixture (M-I) comprising at least 70 wt.-% of water and a mixture (M-II) comprising less than 30 wt.-% of water.

In step (I), a mixture (M") is obtained which can be further separated by means of reverse osmosis.

The present invention therefore also relates to a process for separating at least one propylene glycol from a mixture (M) comprising water and said propylene glycol, said process comprising
  (I) evaporating the mixture in at least two evaporation and/or distillation stages at decreasing operating pressures of the evaporators and/or distillation columns obtaining mixture (M') and mixture (M");
  (II) separating the mixture (M') obtained in (I) in at least one further distillation step, obtaining a mixture (M-I) comprising at least 70 wt.-% of water and a mixture (M-II) comprising less than 30 wt.-% of water;
wherein mixture (M") is further separated into mixture (M-Ia) comprising at least 90 wt.-% of water and mixture (M-Ib) comprising less than 95 wt.-% of water by means of reverse osmosis.

According to step (I), the mixture is evaporated in at least two evaporation and/or distillation stages at decreasing operating pressures of the evaporators and/or distillation columns obtaining mixture (M') and mixture (M"). Preferably, the mixture is evaporated in 2 to 6 evaporation and/or distillation stages at decreasing operating pressures of the evaporators and/or distillation columns, in particular 3, 4 or 5 evaporation and/or distillation stages, preferably 3 evaporation and/or distillation stages. It is also possible to combine the last evaporation or distillation stage according to step (I) with the distillation according to step (II).

The evaporators and/or distillation columns are operated at decreasing operating pressures and temperatures. Preferably a first evaporation or distillation stage is operated at a pressure of 1.5 to 5.5 bar, preferably 2.0 to 5.0 bar, in particular 2.5 to 4.5 bar, for example 2.8, 2.9, 3.0, 3.1, or 3.2 bar; and at a temperature of 111 to 156° C., preferably 120 to 152° C., in particular 127 to 148° C., more preferably 130 to 140° C.

Preferably a second evaporation or distillation stage is operated at a pressure of 1.3 to 5.0 bar, preferably 1.4 to 4.0 bar, in particular 1.5 to 3.0 bar, for example 1.8, 1.9, 2.0, 2.1, or 2.2 bar; and at a temperature of 107 to 152° C., preferably 110 to 144° C., in particular 111 to 134° C., more preferably 118 to 125° C.

Preferably a third evaporation or distillation stage is operated at a pressure of 0.7 to 4.0 bar, preferably 0.8 to 3.0 bar, in particular 0.9 to 2.0 bar, for example 1.0, 1.1, 1.2, 1.3, or 1.4 bar; and at a temperature of 90 to 144° C. preferably 95 to 135° C., in particular 90 to 125° C., more preferably 105 to 115° C.

In case a fourth evaporation or distillation stage is carried out, the fourth evaporation or distillation stage is preferably operated at a pressure of 0.1 to 1.5 bar, preferably 0.2 to 1.2 bar, in particular 0.3 to 1.0 bar, for example 0.4, 0.5, 0.6, 0.7, or 0.8 bar; and at a temperature of 70 to 115° C., preferably 75 to 110° C., in particular 75 to 100° C.

Mixture (M) is treated to a series of evaporation and/or distillation treatments in subsequent stages at progressively lower pressures.

Due to the pressure gradient between subsequent stages there is a resulting decrease in boiling temperature in successive stages. This gradient allows the condensing vapors from one section to be used as the heat medium for the next stage.

Thus, a stage as used in this context is a section of a multi-stage evaporator heated preferably by vapour, preferably steam and also releasing vapor to a subsequent section, where it is used to supply at least part of the evaporation heat needed. The remaining liquid product from one stage is the preferably more concentrated liquid feed to the next stage.

The at least two evaporation and/or distillation stages used for the purpose of the present invention can be operated in a so called forward-feed mode: the raw feed is introduced into the first stage and is passed from stage to stage parallel to the vapour, preferably steam flow, while the liquid "product" is withdrawn from the last stage. It is also possible to operate the evaporation process in a so called counter current mode. Alternatively, the multi-stage evaporation may be carried out in a so called parallel mode, which involves splitting the waste water feed over the different stages of the evaporation train.

In general, a stage will have a vapor outlet and a liquid outlet as well as heating means for providing the evaporation heat. Such heating means could, for instance, be in the form of a reboiler arranged at the liquid (i.e. bottom) part of the stage. Alternatively, heating means can be in the form of heating surfaces like tubes or plates. All such heating means have in common that their heat input is supplied by the vapor from the previous stage. The heat supply for the first stage of a multi-stage evaporator will normally either be provided by fresh steam or by another process stream capable of providing the heat at the right temperature. The steam recovered as the top fraction from the last stage is suitably condensed with cooling water. The condensate stream thus obtained can then be passed to subsequent step, while the condensation heat recovered can be applied elsewhere in the process or removed by a cooling medium.

Generally, all evaporators and distillation columns can be used for the process of the invention. Preferably falling film evaporators as reboilers and towers equipped with trays, especially Thormann trays are used.

According to the present invention, mixture (M) comprises water and propylene glycol. Preferably, the mixture (M) comprises less than 99.9 wt.-% of water, for example 70 to 99.5 wt.-% of water, preferably 80 to 99.0 wt.-% of water, more preferably 90 to 98 wt.-% of water. Mixture (M) further comprises preferably less than 30 wt.-% of propylene glycol, for example 0.01 to 25 wt.-% of propylene glycol, preferably 0.1 to 20 wt.-% of propylene glycol, more preferably 0.5 to 15 wt.-% of propylene glycol, in particular 1.0 to 10 wt.-% of propylene glycol, most preferably 1.5 to 5 wt.-% of propylene glycol.

Mixture (M) can further comprise organic solvents or further organic compounds, preferably in an amount of less than 10 wt.-%, in particular less than 5 wt.-%.

Mixture (M') obtained in step (I) comprises propylene glycol and water. Preferably mixture (M') comprises 80 to 99.9 wt.-% of water and 2.5 to 15 wt.-% of propylene glycol, more preferably 85 to 99.0 wt.-% of water and 5 to 12.5 wt.-% of propylene glycol, in particular 88 to 95 wt.-% of water and 6 to 10 wt.-% of propylene glycol.

Mixture (M") obtained in step (I) comprises at least 70 wt.-% of water. Preferably mixture (M") comprises 90 to 99.99 wt.-% of water and 0.01 to 0.5 wt.-% of propylene glycol, more preferably 95 to 99.9 wt.-% of water and 0.05 to 0.25 wt.-% of propylene glycol, in particular 98 to 99.5 wt.-% of water and 0.07 to 0.1 wt.-% of propylene glycol.

According to step (II), mixture (M') obtained in (I) is separated in at least one further distillation step, obtaining a mixture (M-I) comprising at least 70 wt.-% of water and a mixture (M-II) comprising less than 30 wt.-% of water.

The distillation according to step (II) can be carried out in any suitable distillation column. Preferably a falling film evaporator as reboiler and a tower equipped with trays, especially Thormann trays is used.

Preferably, mixture (M-I) is obtained as top stream and mixture (M-II) is obtained as bottom stream of the distillation.

According to the present invention, mixture (M-I) comprises at least 70 wt.-% of water and a mixture (M-II) comprises less than 30 wt.-% of water. Preferably mixture (M-I) comprises 90 to 99.99 wt.-% of water and 0.01 to 0.5 wt.-% of propylene glycol, more preferably 95 to 99.9 wt.-% of water and 0.05 to 0.25 wt.-% of propylene glycol, in particular 98 to 99.5 wt.-% of water and 0.07 to 0.1 wt.-% of propylene glycol.

Preferably mixture (M-II) comprises 2.5 to 20 wt.-% of water and 50 to 90 wt.-% of propylene glycol, more preferably 5 to 15 wt.-% of water and 60 to 80 wt.-% of propylene glycol, in particular 7 to 12 wt.-% of water and 65 to 75 wt.-% of propylene glycol.

According to the present invention, step (II) of the process according to the present invention can be carried out directly after step (I). It is also possible that mixture (M') obtained in step (I) is further treated before step (II). The mixture can be heated or cooled, or otherwise suitably treated.

It is also possible according to an alternative embodiment that mixture (M') is directly introduced in a separation step by means of reverse osmosis. It is also possible that mixture (M') obtained in step (I) is further treated before the separation step by means of reverse osmosis. The mixture can be heated or cooled, or otherwise suitably treated.

The present invention therefore provides a process for separating at least one propylene glycol from a mixture (M) comprising water and said propylene glycol, said process comprising
(I) evaporating the mixture in at least two evaporation and/or distillation stages at decreasing operating pressures of the evaporators and/or distillation columns obtaining mixture (M') and mixture (M");
(II) separating the mixture (M') obtained in (I) in at least one further distillation step, obtaining a mixture (M-I) comprising at least 70 wt.-% of water and a mixture (M-II) comprising less than 30 wt.-% of water.

According to an alternative embodiment, the present invention relates to a process for separating at least one propylene glycol from a mixture (M) comprising water and said propylene glycol, said process comprising
(I) evaporating the mixture in at least two evaporation and/or distillation stages at decreasing operating pressures of the evaporators and/or distillation columns obtaining mixture (M') and mixture (M");
(II) separating the mixture (M') obtained in (I) in at least one further distillation step, obtaining a mixture (M-I) comprising at least 70 wt.-% of water and a mixture (M-II) comprising less than 30 wt.-% of water;
wherein mixture (M") is further separated into mixture (M-Ia) comprising at least 90 wt.-% of water and mixture (M-Ib) comprising less than 95 wt.-% of water by means of reverse osmosis.

According to an alternative embodiment, the present invention relates to a process for separating at least one propylene glycol from a mixture (M) comprising water and said propylene glycol, said process comprising
(I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water, wherein mixture (M") and mixture (M-I) are combined and further separated into mixture (M-Ia) comprising at least 90 wt.-% of water and mixture (M-Ib) comprising less than 95 wt.-% of water by means of reverse osmosis.

According to another embodiment of the present invention, the process can additionally comprise a step (III):

(III) separating the at least one propylene glycol from the mixture (M-II) in at least one further distillation step.

According to step (III), the at least one propylene glycol is separated from the mixture (M-II) in at least one further distillation step. Preferably, step (III) is carried out using a dividing wall column. In step (III), mixture (M-III) and a mixture containing essentially propylene glycol are obtained. In a preferred embodiment, in step (III), mixture (M-IIIa), mixture (M-IIIb) and a mixture (M-IIIc) containing essentially propylene glycol are obtained. Preferably, mixture (M-III) or mixture (M-IIIa) comprises 10 to 70 wt.-% of water, preferably 15 to 55 wt.-% of water, in particular 20 to 40 wt.-% of water, for example 30 to 35 wt.-% of water.

Preferably the at least one propylene glycol, preferably as mixture (M-IIIc), is obtained in a purity of more than 95%, preferably more than 98%, in particular more than 99%, for example 99.1%, 99.2%, 99.3%, 99.4%, 99.5%, 99.6%, 99.7%, 99.8%, 99.9% or 100%, most preferable in a range of 99.5 to 99.9%. Preferably mixture (M-IIIc) is obtained as a side stream.

The distillation according to step (III) can be carried out in one, two, three or more stages, preferably in one or two stages, more preferably in one stage.

All suitable distillation columns can be used for the distillation according to step (III). Preferably a divided wall column equipped with gauze packing 500 m$^2$/m$^3$ supplied by Koch Glitsch, Montz, Sulzer and a falling film evaporator operated with 16 bar steam.

The distillation column used in step (III) is preferably operated at a pressure of 0.01 to 0.15 bar, preferably 0.03 to 0.10 bar, for example 0.04 bar, 0.05 bar, 0.06 bar, 0.07 bar, 0.08 bar, or 0.09 bar; and a bottom temperature of 120 to 200° C., preferably 140 to 180° C., in particular of 160 to 170° C.

Preferably, propylene glycol, preferably as mixture (M-IIIc), is obtained as a side stream of the distillation. Preferably, mixture (M-IIIa) is obtained as a top stream of the distillation. It is also possible in the context of the present invention that further streams are obtained such as bottom streams. Preferably mixture (M-IIIb) is obtained as bottom stream.

According to the present invention, step (III) of the process according to the present invention can be carried out directly after step (II). It is also possible that mixture (M-II) obtained in step (II) is further treated before step (III). The mixture can be heated or cooled, or otherwise suitably treated. It is also possible that mixture (M-II) is combined with at least one other mixture obtained in the process according to the present invention before step (III).

Therefore, the present invention also provides a process as described above, wherein the process additionally comprises the step (III) separating the at least one propylene glycol from the mixture (M-II) in at least one further distillation step.

According to the present invention, the mixture (M-I) obtained in step (II) can be further separated into mixture (M-Ia) comprising at least 90 wt.-% of water and mixture (M-Ib) comprising less than 95 wt.-% of water by means of reverse osmosis.

According to the present invention, it is also possible that mixture (M") obtained in step (I) is directly subjected to a further separation step by means of reverse osmosis. In this case, mixture (M") is separated into mixture (M-Ia) comprising at least 90 wt.-% of water and mixture (M-Ib) comprising less than 95 wt.-% of water by means of reverse osmosis.

It is also possible to combine mixture (M") and mixture (M-I) and then subject the combined mixtures to a separation by means of reverse osmosis.

The separation step by means of reverse osmosis is preferably carried out at an operating pressure of from 30 to 120 bar, preferably of from 60 to 110 bar, more preferred of from 80 to 100 bar, especially of about 90 bar. The separation step by means of reverse osmosis is preferably carried out at a temperature of from 20 to 80° C., more preferred of from 30 to 60° C., preferably of from 35 to 45° C. especially of about 38 to 42° C., for example 39° C., 40° C., or 41° C.

According to the present invention, the separation step by means of reverse osmosis is preferably carried out using 2 to 8 stages. Reverse osmosis is preferably carried out using 2 to 8 modules stages connected in parallel, preferrably using 4 to 6 modules stages, for example 5 modules stages.

In each stage, the ratio of feed to retentate is preferably about 20 to about 60, for example 25 to 55 or 50.

Preferably, one of four different types of reverse osmosis modules, which are generally used for reverse osmosis processes, is used for the process of the present invention. Preferably, tubular, plate and frame, spiral, and hollow fiber modules are used.

Tubular membranes are not self-supporting membranes. They are located on the inside of a tube, made of a material which is the supporting layer for the membrane. Because the location of tubular membranes is inside a tube, the flow in a tubular membrane is usually inside out. Tubular membranes generally have a diameter of about 5 to 15 mm.

With capillary membranes the membrane serves as a selective barrier, which is sufficiently strong to resist filtration pressures. Because of this, the flow through capillary membranes can be both inside out and outside in. The diameter of capillary membranes is much smaller than that of tubular membranes, namely 0.5 to 5 mm. Because of the smaller diameter the chances of plugging are much higher with a capillary membrane.

Spiral membranes consist of two layers of membrane, placed onto a permeate collector fabric. This membrane envelope is wrapped around a centrally placed permeate drain. This causes the packing density of the membranes to be higher. The feed channel is placed at moderate height, to prevent plugging of the membrane unit.

The pressurized mixture flows along the external surface of the membrane sleeves. A solution penetrates and flows within the spiral sleeve towards the central pipe that leads it out of the module.

Membranes that consist of flat plates are called pillow-shaped membranes. The name pillow-shaped membrane comes from the pillow-like shape that two membranes have when they are packed together in a membrane unit. Inside the 'pillow' is a supporting plate, which attends solidity.

Within a module, multiple pillows are placed with a certain distance between them, which depends on the dissolved solids content of the solution. The solution flows through the membranes inside out. When treatment is done, the permeate is collected in the space between the membranes, where it is carried away through drains.

Hollow fiber membranes are membranes with a diameter of below about 0.1 μm.

As membranes, all membranes with a sufficient stability against organic compounds for example membranes having a celluloseacetate, composite or polyamid active layer can be used. Preferably membranes with polyamid active layer as spiral membrane modules are used.

According to a preferred embodiment of the present invention, the mixture (M-I) obtained in step (II)—or according to an alternative embodiment mixture (M'') obtained in step (I) or mixture (M'') combined with mixture (M-I)—can be separated into mixture (M-Ia) comprising at least 90 wt.-% of water and mixture (M-Ib) comprising less than 95 wt.-% of water by means of reverse osmosis.

Mixture (M-Ia) comprises at least 90 wt.-% of water. Preferably mixture (M-Ia) comprises at least 95 wt.-% of water, more preferably at least 98 wt.-% of water, in particular at least 99 wt.-% of water, for example 99.3 wt.-%, 99.4 wt.-%, 99.5 wt.-%, 99.6 wt.-%, 99.7 wt.-%, 99.8 wt.-%, 99.9 wt.-% or 99.99 wt.-%, most preferable in a range of 99.8 to 99.95 wt.-%.

Mixture (M-Ia) preferably comprises less than 1 wt.-% of other organic or inorganic compounds, more preferably less than 0.5 wt.-%, in particular less than 0.25 wt.-%.

Mixture (M-Ib) comprises less than 95 wt.-% of water. Preferably mixture (M-Ib) comprises 80 to 95 wt.-% of water, in particular 82 to 92 wt.-% of water, more preferably 85 to 90 wt.-% of water. Mixture (M-Ib) further comprises less than 25 wt.-% of other organic or inorganic compounds, preferably 1 to 20 wt.-%, in particular 2.5 to 15 wt.-%, more preferably 5 to 10 wt.-%.

Therefore, the present invention also provides a process as described above, wherein mixture (M-I) or mixture (M'') or mixture (M'') combined with mixture (M-I) is further separated into mixture (M-Ia) comprising at least 90 wt.-% of water and mixture (M-Ib) comprising less than 95 wt.-% of water by means of reverse osmosis.

According to the present invention, the process as described above can also comprise step (III) and additionally the separation by reverse osmosis.

Therefore, the present invention also provides a process as described above, wherein mixture (M-I) is further separated into mixture (M-Ia) comprising at least 90 wt.-% of water and mixture (M-Ib) comprising less than 95 wt.-% of water by means of reverse osmosis, and the process additionally comprises the step (III) separating the at least one propylene glycol from the mixture (M-II) in at least one further distillation step.

Mixture (I-b) comprises preferably less than 5 wt.-% of organic compounds such as mono propylene glycol, dipropylene glycol, methoxypropanols, or hydroxyacetone.

Therefore, according to another embodiment of the present invention, this mixture (MIb) can be combined with mixture (M-II) prior to step (III), therefore preferably resulting in an improved yield of propylene glycol.

Therefore, the present invention also provides a process as described above, wherein mixture (M-Ib) and mixture (M-II) are combined prior to step (III).

According to the present invention, in step (I), the mixture is evaporated in 2 to 6 evaporation and/or distillation stages at decreasing operating pressures of the evaporators and/or distillation columns, in particular 3 to 5 evaporation and/or distillation stages, preferably 3 or 4 evaporation and/or distillation stages.

Therefore, the present invention also provides a process as described above, wherein in step (I) three evaporation stages (E1) to (E3) or three distillation stages (D1) to (D3) are carried out.

Preferably the three evaporation stages are carried out at decreasing operating pressures.

Preferably the three evaporation stages are carried out at decreasing operating pressures in the ranges of 1.5 to 5.5 bar at a temperature of 111 to 156° C., 1.3 to 5.0 bar at a temperature of 107 to 152° C., 0.7 to 4.0 bar at a temperature of 90 to 144° C.

Therefore, the present invention also provides a process as described above, wherein the three evaporation stages according to step (I) are carried out at decreasing operating pressures in the ranges (E1) 1.5 to 5.5 bar at a temperature of 111 to 155° C.,
(E2) 1.3 to 5.0 bar at a temperature of 107 to 152° C.,
(E3) 0.7 to 4.0 bar at a temperature of 90 to 144° C.

The present invention also provides a process as described above, wherein the three distillation stages according to step (I) are carried out at decreasing operating pressures in the ranges (D1) 1.5 to 5.5 bar at a temperature of 111 to 155° C.,
(D2) 1.3 to 5.0 bar at a temperature of 107 to 152° C.,
(D3) 0.7 to 4.0 bar at a temperature of 90 to 144° C.

According to the present invention, mixture (M) comprises at least one propylene glycol. Preferably, mixture (M) comprises at least one propylene glycol in an amount of less than 30 wt.-%, for example 0.01 to 25 wt.-%, preferably 0.1 to 20 wt.-%, more preferably 0.5 to 15 wt.-%, in particular 1.0 to 10 wt.-%, most preferably 1.5 to 5 wt.-%.

Therefore, the present invention also provides a process as described above, wherein the mixture (M) comprises 0.01 to 25 wt.-% propylene glycol.

For example, mixture (M) can further comprise hydroxyaceton in an amount of about 0.2 wt.-% and dipropylene glycol in an amount of about 0.4 wt.-%.

Suitable mixtures can for example be obtained as by-products of industrial processes, for example in an epoxidation of propene. Preferably, mixture (M) is obtained as a by-product in a process for the epoxidation of propene. In the framework of the present invention it is also possible, that any mixture obtained as a by-product in a process for the epoxidation of propene is further treated before being introduced in step (I) of the process according to the present invention.

Therefore, the present invention also provides a process as described above, wherein the mixture (M) is obtained as a by-product in a process for the epoxidation of propene.

Preferably, the epoxidation of propene is carried out using a hydroperoxide in the presence of a catalyst.

According to a further embodiment of the present invention, mixture (M) may be obtained as a by-product in a process for the epoxidation of propene. Preferably, the process for the epoxidation of propen comprises a stage (a)

(a) reacting propylene with a hydroperoxide in the presence of at least one solvent and at least one catalyst to obtain a mixture (M-a) comprising propylene oxide.

Therefore, the present invention also provides a process as described above, wherein the mixture (M) is obtained as a by-product in a process for the epoxidation of propylene comprising the stage (a) reacting propylene with a hydroperoxide in the presence of at least one solvent and at least one catalyst to obtain a mixture (M-a) comprising propylene oxide.

In the context of the present invention, the term "hydroperoxide" refers to a compound of the formula ROOH. Details regarding the preparation of hydroperoxides and regarding hydroperoxides which can be used, inter alia, in the method of the present invention may be found in DE-A-198 35 907 the respective content of which is incorporated in the context of the present invention by reference. Examples of hydroperoxides which can be used for the purposes of the present invention are, inter alia, tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronaphthalene hydroperoxide, isobutylbenzene hydroperoxide, ethylnaphthalene hydroperoxide, peracids such as peracetic acid and hydrogen peroxide. Mixtures of two or more hydroperoxides can also be used according to the present invention. Preference is given to using hydrogen peroxide as hydroperoxide in the method of the present invention, and further preference is given to using an aqueous hydrogen peroxide solution. Most preferably, the aqueous hydrogen peroxide solution comprises hydrogen peroxide in a concentration in the range of from 1 to 90, more preferably of from 10 to 70 and especially preferably of from 30 to 50 wt.-%, based on the total weight of the solution. It is also possible to use a mixture of two or more different hydroperoxides.

Preferably, hydrogen peroxide is used as the hydroperoxide.

Therefore, the present invention also provides a process as described above, wherein in stage (a) the hydroperoxide is hydrogen peroxide.

According to stage (a), propylene is reacted with a hydroperoxide to obtain a mixture (M-a) comprising propylene oxide.

According to stage (a) of the process, propylene is reacted with a hydroperoxide in the presence of a solvent. According to the present invention, all suitable solvents known to the person skilled in the art can be used. A suitable solvent is for example methanol.

Therefore, the present invention also provides a process as described above, wherein in stage (a) the solvent is methanol.

The reaction according to stage (a) can be carried out in one or more stages. It is also possible to separate off one or more components of the reaction mixture between the reaction stages. It is also possible to add one or more components to the reaction mixture between the individual reaction stages.

Accordingly, it is possible to carry out one of the reactions stages in batch mode or in semi-continuous mode or in continuous mode and independently thereof, the other reaction stage in batch mode or in semi-continuous mode or in continuous mode.

The epoxidation reaction in stages (a) is preferably carried out in the presence of at least one zeolite catalyst.

Therefore, the present invention also provides a process as described above, wherein in stage (a) the catalyst is at least one titanium zeolite catalyst.

Preferably, in stage (a) at least one titanium zeolite catalyst is used as a catalyst and the solvent is methanol.

Therefore, the present invention also provides a process as described above, wherein in stage (a) the catalyst is at least one titanium zeolite catalyst and the solvent is methanol.

Zeolites are, as is known, crystalline aluminosilicates having ordered channel and cage structures and containing micropores which are preferably smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolite Structure Types", Elsevier, 5th edition, Amsterdam 2001.

Zeolites in which no aluminum is present and in which part of the Si(IV) in the silicate lattice is replaced by titanium as Ti(IV) are also known. These titanium zeolites, in particular those having a crystal structure of the MFI type, and possible ways of preparing them are described, for example, in EP 0 311 983 A2 or EP 0 405 978 A1. Apart from silicon and titanium, such materials can further comprise additional elements such as aluminum, zirconium, tin, iron, cobalt, nickel, gallium, germanium, boron or small amounts of fluorine. In the zeolite catalysts which have preferably been regenerated by the process of the invention, part or all of the titanium of the zeolite can have been replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Titanium zeolites, in particular those having a crystal structure of the MFI type, and possible ways of preparing them are described, for example, in WO 98/55228, EP 0 311 983 A2, EP 0 405 978 A1, EP 0 200 260 A2.

It is known that titanium zeolites having the MFI structure can be identified via a particular X-ray diffraction pattern and also via a lattice vibration band in the infrared (IR) region at about 960 $cm^{-1}$ and thus differ from alkali metal titanates or crystalline and amorphous $TiO_2$ phases.

Specific mention may be made of titanium-, germanium-, tellurium-, vanadium-, chromium-, niobium-, zirconium-containing zeolites having a pentasil zeolite structure, in particular the types which can be assigned X-ray-crystallographically to the structures ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG and ZON, and also mixed structures of two or more of the abovementioned structures. Furthermore, titanium-containing zeolites having the ITQ-4, SSZ-24, TTM-1, UTD-1, CIT-1 or CIT-5 structure are also conceivable for use in the process of the invention. Further titanium-containing zeolites which may be mentioned are those having the ZSM-48 or ZSM-12 structure.

For the purposes of the present invention, preference is given to using Ti zeolites having an MFI structure, an MEL structure, an MFI/MEL mixed structure or an MWW structure. Further preference is given specifically to the Ti-containing zeolite catalysts which are generally referred to as "TS-1", "TS-2", "TS-3", and also Ti zeolites having a framework structure isomorphous with beta-zeolite. Very particular preference is given to using zeolite catalysts of the TS-1 structure and the Ti-MWW structure.

The catalysts, especially preferably the titanium zeolite catalysts and still more preferably the catalysts having TS1 or MWW structure, can be employed as powder, as granules, as microspheres, as shaped bodies having, for example, the shape of pellets, cylinders, wheels, stars, spheres and so forth, or as extrudates such as extrudates having, for example, a length of from about 1 to 10, more preferably of from 1 to 7 and still more preferably of from 1 to 5 mm, and a diameter of from about 0.1 to 5, more preferably of from 0.2 to 4 and especially preferably of from 0.5 to 2 mm. In order to increase the bulk density of the extrudates, it is preferred to cut the extrudates with a stream essentially consisting of an inert gas.

For each of these forming methods, it is possible to use at least one additional binder and/or at least one pasting agent and/or at least one pore forming agent. Prior to using the catalyst in the epoxidation reaction of the present invention, it is possible to suitably pretreat the catalyst. In case the catalyst is used as supported catalyst, a carrier can be preferably used which are inert, i.e. which do not react with hydrogen peroxide, olefin, and olefin oxide.

Most preferably, a Ti-TS1 or Ti-MWW catalyst is employed which is produced by first forming microspheres, for example microspheres formed according to EP 0 200 260 A2, and then forming said microspheres to obtain shaped bodies, preferably extrudates as described above.

Therefore, the reactions in stages (a) are preferably carried out in suspension or fixed-bed mode, most preferably in fixed-bed mode.

It is possible to carry out one of the reactions stages in an isothermal or adiabatic reactor and the other reaction stage, independently thereof, in an isothermal or adiabatic reactor. The term "reactor" as used in this respect comprises a single reactor, a cascade of at least two serially connected reactors, at least two reactors which are operated in parallel, or a multitude of reactors wherein at least two reactors are serially coupled and wherein at least two reactors are operated in parallel.

Each of the reactors described above, especially the reactors according to the preferred embodiment, can be operated in downflow or in upflow operation mode.

In case the reactors are operated in downflow mode, it is preferred to use fixed-bed reactors which are preferably tubular, multi-tubular or multi-plate reactors, most preferably equipped with at least one cooling jacket. In this case, the epoxidation reaction is carried out at a temperature of from 30 to 80° C., and the temperature profile in the reactors is maintained at a level so that the temperature of the cooling medium in the cooling jackets is at least about 40° C. and the maximum temperature in the catalyst bed is about 60° C. In case of downflow operation of the reactors, it is possible to chose the reaction conditions such as temperature, pressure, feed rate and relative amounts of starting materials such that the reaction is carried out in a single phase, more preferably in a single liquid phase, or in a multiphase system comprising, for example, 2 or 3 phases. As to the downflow operation mode, it is especially preferred to conduct the epoxidation reaction in a multiphase reaction mixture comprising a liquid aqueous hydrogen peroxide rich phase containing methanol and a liquid organic olefin rich phase, preferably a propene rich phase.

In case the reactors are operated in upflow mode, it is preferred to use fixed-bed reactors. It is still further preferred to use at least two fixed-bed reactors. According to a still further embodiment, the at least two reactors used are serially connected or operated in parallel, more preferably operated in parallel. Generally, it is necessary to equip at least one of the reactors used with a cooling means such as a cooling jacket. Especially preferably, at least two reactors are employed which are connected in parallel and can be operated alternately. In case the reactors are operated in upflow mode, the two or more reactors connected in parallel are particularly preferably tube reactors, multi-tube reactors or multi-plate reactors, more preferably multi-tube reactors and especially preferably shell-and-tube reactors comprising a multitude of tubes such as from about 1 to 20 000, preferably from 10 to 10 000, more preferably from 100 to 9000, more preferably from 1000 to 8000 and particularly preferably from 3000 to 7000, tubes. To regenerate the catalyst used for the epoxidation reaction, it is possible for at least one of the reactors connected in parallel to be taken out of operation for the respective reaction stage and the catalyst present in this reactor to be regenerated, with at least one reactor always being available for reaction of the starting material or starting materials in every stage during the course of the continuous process.

As cooling medium used for cooling the reaction media in above-mentioned reactors equipped with cooling jackets, there are no specific restrictions. Especially preferred are oils, alcohols, liquid salts or water, such as river water, brackish water and/or sea water, which can in each case, for example, preferably be taken from a river and/or lake and/or sea close to the chemical plant in which the reactor of the invention and the process of the invention are used and, after any necessary suitable removal of suspended material by filtration and/or sedimentation, be used directly without further treatment for cooling the reactors. Secondary cooling water which is preferably conveyed around a closed circuit is particularly useful for cooling purposes. This secondary cooling water is generally essentially deionized or demineralised water to which at least one antifouling agent has preferably been added. More preferably, this secondary cooling water circulates between the reactor of the invention and, for example, a cooling tower. Preference is likewise given to the secondary cooling water being, for example, countercooled in at least one countercurrent heat exchanger by, for example, river water, brackish water and/or sea water.

According to a preferred embodiment, the hydrogen peroxide is used in the process according to the invention in the form of an aqueous solution with a hydrogen peroxide content of generally of from 1 to 90 wt.-%, preferably of from 10 to 70 wt.-%, more preferably from 10 to 60 wt.-%. A solution having of from 20 to less than 50 wt.-% of hydrogen peroxide is particularly preferred.

According to another embodiment of the present invention, a crude aqueous hydrogen peroxide solution can be employed. As crude aqueous hydrogen peroxide solution, a solution can be used which is obtained by extraction of a mixture with essentially pure water wherein the mixture results from a process known as anthrachinone process (see, e.g., Ullmann's Encycolpedia of Industrial Chemistry, 5th edition, volume 3 (1989) pages 447-457). In this process, the hydrogen peroxide formed is generally separated by extraction from the working solution. This extraction can be performed with essentially pure water, and the crude aqueous hydrogen peroxide is obtained. According to one embodiment of the present invention, this crude solution can be employed without further purification. The production of such a crude solution is described, for example, in European patent application EP 1 122 249 A1. As to the term "essentially pure water", reference is made to paragraph 10, page 3 of EP 1 122 249 A1 which is incorporated by reference.

To prepare the hydrogen peroxide which is preferably used, it is possible to employ, for example, the anthraquinone process by means of which virtually the entire world production of hydrogen peroxide is produced. An overview of the anthraquinone process is given in "Ullmann's Encyclopedia of Industrial Chemistry", 5th edition, volume 13, pages 447 to 456.

It is likewise conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid which is thus obtained back.

Of course, the preparation of hydrogen peroxide from the elements is also possible.

Before hydrogen peroxide is used in the process of the invention, it is possible to free, for example, a commercially available hydrogen peroxide solution of undesirable ions. Conceivable methods are, inter alia, those described, for example, in U.S. Pat. No. 5,932,187, DE 42 22 109 A1 or U.S. Pat. No. 5,397,475. It is likewise possible to remove at least one salt present in the hydrogen peroxide solution from the hydrogen peroxide solution by means of ion exchange in an apparatus which contains at least one nonacidic ion exchanger bed having a flow cross-sectional area F and a height H which are such that the height H of the ion exchanger bed is less than or equal to $2.5 \cdot F^{1/2}$, in particular less than or equal to $1.5 \cdot F^{1/2}$. For the purposes of the present invention, it is in principle possible to use all nonacidic ion exchanger beds comprising cation exchangers and/or anion exchangers. It is also possible for cation and anion exchangers to be used as mixed beds within one ion exchanger bed. In a preferred embodiment of the present invention, only one type of nonacidic ion exchangers is used. Further preference is given to the use of basic ion exchange, particularly preferably that of a basic anion exchanger and more particularly preferably that of a weakly basic anion exchanger.

The selectivity of the overall process according to stage (a) in respect of hydrogen peroxide is preferably in the range from 78 to 99%, more preferably in the range from 88 to 97% and particularly preferably in the range from 90 to 96%.

The total hydrogen peroxide conversion is preferably at least 99.5%, more preferably at least 99.6%, more preferably at least 99.7% and particularly preferably at least 99.8%.

The mixture (M-a) obtained in stage (a) preferably has a solvent, preferably a methanol content of from 50 to 90 wt.-%, more preferably of from 60 to 85 wt.-% and especially preferably of from 70 to 80 wt.-%, based on the total weight of the reaction mixture. It further can contain water, propylene oxide, or propene.

The mixture (M-a) obtained from stage (a) has to be suitably treated to obtain mixture (M).

Mixture (M) according to the present invention is essentially free of an organic solvent such as methanol, and propene or propylene oxide. Mixture (M-a) can be suitably treated to separate of any organic solvent, propylene or propylene oxide. Suitable methods for separating of solvent, propylene or propylene oxide are known to the person skilled in the art.

It is for example possible to separate off unreacted propylene from the mixture (M-a) by distillation in a stage (b).

It is also possible to separate off propylene oxide from the mixture by distillation in a stage (c), preferably after the separation of the unreacted propylene.

Preferably, after these two separations according to stages (b) and (c), the mixture comprises water and the solvent, preferably methanol.

The mixture obtained can further contain certain by-products resulting from one or more stages of the overall epoxidation process, having boiling points lower than the propylene oxide. Examples for such by-products are aldehydes such as, for example, acetaldehyde and/or formaldehyde. These by-products can be contained in an amount of up to 0.3 wt.-%, preferably up to 0.20 wt.-% and especially preferably up to 0.15 wt.-%, based on the total weight of the mixture and referring to the sum of the respective weights of these low-boiling compounds.

The mixture comprising water and a solvent, preferably methanol, can be further separated in a further distillative separation process in a stage (d) in which a mixture (M-di) comprising at least 85 wt.-% of methanol and up to 10 wt.-% of water, and a second mixture (M-dii) comprising at least 90 wt.-% of water are obtained.

Distillation in stage (d) can be performed in one, two, three or more distillation columns.

The mixture (M-dii) comprises at least 90 wt.-% of water, more preferably at least 95 wt.-% of water and especially preferably at least 97 wt.-% of water. Preferably (M-dii) is essentially free of methanol, i.e. it has a methanol content of less than 5 ppm, more preferably of less than 1 ppm. Additionally to water, (M-dii) can comprise certain byproducts resulting from one or more stages of the overall epoxidation process. Examples for such by-products are glycol compounds such as propylene glycols. These byproducts can be contained in (M-dii) in an amount of up to 4 wt.-%, preferably up to 3 wt.-%.

According to the process of the present invention, it is possible that the mixture introduced into stage (d) comprises by-produces produced in at least one stage of the overall epoxidation process such as glycol ethers like methoxypropanols.

Stages (b), (c) and (d) can be applied to mixture (M-a) separately or in combination. Preferably, mixture (M-a) is first subjected to stage (b), the resulting mixture is subjected to stage (c) and the mixture resulting from stage (c) is subjected to stage (d). Furthermore, it is possible to treat the resulting mixtures between the stages (a), (b), (c) and (d), for example heat them or add or separate off any further components.

Preferably, a steam which has been treated according to stage (a), (b), (c), and (d) is used as mixture (M) for the process according to the present invention.

In the following, further preferred embodiments of the present invention are described.

According to a preferred embodiment, the present invention also relates to a process for separating at least one propylene glycol from a mixture (M) comprising water and said propylene glycol, said process comprising
(I) evaporating the mixture in at least two evaporation and/or distillation stages at decreasing operating pressures of the evaporators and/or distillation columns obtaining mixture (M') and mixture (M");
(II) separating the mixture (M') obtained in (I) in at least one further distillation step, obtaining a mixture (M-I) comprising at least 70 wt.-% of water and a mixture (M-II) comprising less than 30 wt.-% of water;
(III) separating the at least one propylene glycol from the mixture (M-II) in at least one further distillation step.

According to a further preferred embodiment, the present invention also relates to a process for separating at least one propylene glycol from a mixture (M) comprising water and said propylene glycol, said process comprising
(I) evaporating the mixture in at least two evaporation and/or distillation stages at decreasing operating pressures of the evaporators and/or distillation columns obtaining mixture (M') and mixture (M");
(II) separating the mixture (M') obtained in (I) in at least one further distillation step, obtaining a mixture (M-I) comprising at least 70 wt.-% of water and a mixture (M-II) comprising less than 30 wt.-% of water, wherein mixture (M-I) is further separated into mixture (M-Ia) comprising at least 90 wt.-% of water and mixture (M-Ib) comprising less than 95 wt.-% of water by means of reverse osmosis.

According to a still further preferred embodiment, the present invention also relates to a process for separating at least one propylene glycol from a mixture (M) comprising water and said propylene glycol, said process comprising
- (I) evaporating the mixture in at least two evaporation and/or distillation stages at decreasing operating pressures of the evaporators and/or distillation columns obtaining mixture (M') and mixture (M");
- (II) separating the mixture (M') obtained in (I) in at least one further distillation step, obtaining a mixture (M-I) comprising at least 70 wt.-% of water and a mixture (M-II) comprising less than 30 wt.-% of water;
- (III) separating the at least one propylene glycol from the mixture (M-II) in at least one further distillation step, wherein mixture (M-I) is further separated into mixture (M-Ia) comprising at least 90 wt.-% of water and mixture (M-Ib) comprising less than 95 wt.-% of water by means of reverse osmosis.

According to a still further preferred embodiment, the present invention also relates to a process for separating at least one propylene glycol from a mixture (M) comprising water and said propylene glycol, said process comprising
- (I) evaporating the mixture in at least two evaporation and/or distillation stages at decreasing operating pressures of the evaporators and/or distillation columns obtaining mixture (M') and mixture (M");
- (II) separating the mixture (M') obtained in (I) in at least one further distillation step, obtaining a mixture (M-I) comprising at least 70 wt.-% of water and a mixture (M-II) comprising less than 30 wt.-% of water, wherein the mixture (M) is obtained as a by-product in a process for the epoxidation of propylene comprising the step
- (a) reacting propylene with a hydroperoxide in the presence of at least one solvent and at least one catalyst to obtain a mixture (M-a) comprising propylene oxide.

According to a still further preferred embodiment, the present invention also relates to a process for separating at least one propylene glycol from a mixture (M) comprising water and said propylene glycol, said process comprising
- (I) evaporating the mixture in at least two evaporation and/or distillation stages at decreasing operating pressures of the evaporators and/or distillation columns obtaining mixture (M') and mixture (M");
- (II) separating the mixture (M') obtained in (I) in at least one further distillation step, obtaining a mixture (M-I) comprising at least 70 wt.-% of water and a mixture (M-II) comprising less than 30 wt.-% of water, wherein in step (I) three evaporation stages (E1) to (E3) are carried out at decreasing operating pressures in the ranges
- (E1) 1.5 to 5.5 bar at a temperature of 111 to 155° C.,
- (E2) 1.3 to 5.0 bar at a temperature of 107 to 152° C.,
- (E3) 0.7 to 4.0 bar at a temperature of 90 to 144° C.

According to a still further preferred embodiment, the present invention also relates to a process for separating at least one propylene glycol from a mixture (M) comprising water and said propylene glycol, said process comprising
- (I) evaporating the mixture in at least two evaporation and/or distillation stages at decreasing operating pressures of the evaporators and/or distillation columns obtaining mixture (M') and mixture (M");
- (II) separating the mixture (M') obtained in (I) in at least one further distillation step, obtaining a mixture (M-I) comprising at least 70 wt.-% of water and a mixture (M-II) comprising less than 30 wt.-% of water;
- (III) separating the at least one propylene glycol from the mixture (M-II) in at least one further distillation step;

wherein in step (I) three evaporation stages (E1) to (E3) are carried out at decreasing operating pressures in the ranges
- (E1) 1.5 to 5.5 bar at a temperature of 111 to 155° C.,
- (E2) 1.3 to 5.0 bar at a temperature of 107 to 152° C.,
- (E3) 0.7 to 4.0 bar at a temperature of 90 to 144° C.

According to a still further preferred embodiment, the present invention also relates to a process for separating at least one propylene glycol from a mixture (M) comprising water and said propylene glycol, said process comprising
- (I) evaporating the mixture in at least two evaporation and/or distillation stages at decreasing operating pressures of the evaporators and/or distillation columns obtaining mixture (M') and mixture (M");
- (II) separating the mixture (M') obtained in (I) in at least one further distillation step, obtaining a mixture (M-I) comprising at least 70 wt.-% of water and a mixture (M-II) comprising less than 30 wt.-% of water;
- (III) separating the at least one propylene glycol from the mixture (M-II) in at least one further distillation step, wherein mixture (M-I) is further separated into mixture (M-Ia) comprising at least 90 wt.-% of water and mixture (M-Ib) comprising less than 95 wt.-% of water by means of reverse osmosis, and wherein in step (I) three evaporation stages (E1) to (E3) are carried out at decreasing operating pressures in the ranges
- (E1) 1.5 to 5.5 bar at a temperature of 111 to 155° C.,
- (E2) 1.3 to 5.0 bar at a temperature of 107 to 152° C.,
- (E3) 0.7 to 4.0 bar at a temperature of 90 to 144° C.

According to a still further preferred embodiment, the present invention also relates to a process for separating at least one propylene glycol from a mixture (M) comprising water and said propylene glycol, said process comprising
- (I) evaporating the mixture in at least two evaporation and/or distillation stages at decreasing operating pressures of the evaporators and/or distillation columns obtaining mixture (M') and mixture (M");
- (II) separating the mixture (M') obtained in (I) in at least one further distillation step, obtaining a mixture (M-I) comprising at least 70 wt.-% of water and a mixture (M-II) comprising less than 30 wt.-% of water;

wherein mixture (M-I) is further separated into mixture (M-Ia) comprising at least 90 wt.-% of water and mixture (M-Ib) comprising less than 95 wt.-% of water by means of reverse osmosis;

wherein the mixture (M) is obtained as a by-product in a process for the epoxidation of propylene comprising the step
- (a) reacting propylene with a hydroperoxide in the presence of at least one solvent and at least one catalyst to obtain a mixture (M-a) comprising propylene oxide; and wherein in step (I) three evaporation stages (E1) to (E3) are carried out at decreasing operating pressures in the ranges
- (E1) 1.5 to 5.5 bar at a temperature of 111 to 155° C.,
- (E2) 1.3 to 5.0 bar at a temperature of 107 to 152° C.,
- (E3) 0.7 to 4.0 bar at a temperature of 90 to 144° C.

In the following, preferred processes of the present invention are listed resulting from the following embodiments 1 to 13 including the combinations of these embodiments as explicitly given.

1. A process for separating at least one propylene glycol from a mixture (M) comprising water and said propylene glycol, said process comprising
- (I) evaporating the mixture in at least two evaporation and/or distillation stages at decreasing operating pressures of the evaporators and/or distillation columns obtaining mixture (M') and mixture (M");

(II) separating the mixture (M') obtained in (I) in at least one further distillation step, obtaining a mixture (M-I) comprising at least 70 wt.-% of water and a mixture (M-II) comprising less than 30 wt.-% of water.

2. The process of embodiment 1, wherein mixture (M") is further separated into mixture (M-Ia) comprising at least 90 wt.-% of water and mixture (M-Ib) comprising less than 95 wt.-% of water by means of reverse osmosis.

3. The process of embodiment 1 or 2, wherein the process additionally comprises the step
    (III) separating the at least one propylene glycol from the mixture (M-II) in at least one further distillation step.

4. The process of any of embodiments 1 to 3, wherein mixture (M-I) is further separated into mixture (M-Ia) comprising at least 90 wt.-% of water and mixture (M-Ib) comprising less than 95 wt.-% of water by means of reverse osmosis.

5. The process of any of embodiments 1 to 4, wherein mixture (M") and mixture (M-I) are combined and further separated into mixture (M-Ia) comprising at least 90 wt.-% of water and mixture (M-Ib) comprising less than 95 wt.-% of water by means of reverse osmosis.

6. The process of any of embodiments 1 to 5, wherein mixture (M-Ib) and mixture (M-II) are combined prior to step (III).

7. The process of any of embodiments 1 to 6, wherein in step (I) three evaporation stages (E1) to (E3) or three distillation stages (D1) to (D3) are carried out.

8. The process of embodiment 7, wherein the three evaporation stages according to step (I) are carried out at decreasing operating pressures in the ranges
    (E1) 1.5 to 5.5 bar at a temperature of 111 to 155° C.,
    (E2) 1.3 to 5.0 bar at a temperature of 107 to 152° C.,
    (E3) 0.7 to 4.0 bar at a temperature of 90 to 144° C.

9. The process of any of embodiments 1 to 8, wherein the mixture (M) comprises 0.01 to 25 wt.-% propylene glycol.

10. The process of any of embodiments 1 to 9, wherein the mixture (M) is obtained as a by-product in a process for the epoxidation of propene.

11. The process of any of embodiments 1 to 10, wherein the mixture (M) is obtained as a by-product in a process for the epoxidation of propylene comprising the stage
    (a) reacting propylene with a hydroperoxide in the presence of at least one solvent and at least one catalyst to obtain a mixture (M-a) comprising propylene oxide.

12. The process of embodiment 11, wherein in stage (a) the hydroperoxide is hydrogen peroxide.

13. The process of embodiment 11 or 12, wherein in stage (a) the catalyst is at least one titanium zeolite catalyst and the solvent is methanol.

The invention is illustrated with the following examples.

EXAMPLES

Example 1

Distillation Combined with Reverse Osmosis

From a storage tank, 1000 kg/h of a waste stream from a process for preparing propylene oxide with the following composition

| | |
|---|---|
| water | 97.45 wt.-%, |
| methoxypropanole (MOP) | 0.05 wt.-%, |
| hydroxyaceton (HA) | 0.09 wt.-%, |
| monopropylenglycol (MPG) | 2.04 wt.-%, |
| dipropylenglycolmonomethylether (DPGME) | 0.32 wt.-%, |
| heavy boiling compounds (HBC) | 0.05 wt.-%, | is subjected to distillation in four successive columns which are thermally coupled. The streams obtained at the top of the distillation columns with a water content of about 99.6 to 99.7 wt.-% are mixed together, cooled down to 40° C. and subjected to reverse osmosis (polyamid membrane, spiral modules, with a membrane area of 96 m$^2$, operating pressure 90 bar, T=40° C.). The retentate obtained after reverse osmosis and the bottoms of the last distillation column are combined and subjected to further treatment.

The columns are coupled in a way, that the first column is heated with steam and each of the following columns is heated with the vapors of the column before.

The columns are operated at the following pressures and reflux ratios (RR):

| | | |
|---|---|---|
| Column 1 (diameter 0.3 m, 8 m high, 7 trays): | 3.1 bar | RR = 0.13 |
| Column 2 (diameter 0.3 m, 8 m high, 7 trays): | 2.0 bar | RR = 0.12 |
| Column 3 (diameter 0.3 m, 8 m high, 7 trays): | 1.1 bar | RR = 0.15 |
| Column 4 (diameter 0.6 m, 8 m high, 8 trays): | 95 mbar | RR = 0.25 |

For the above stream of 1 t/h, 175 KW steam are needed for the distillation.

The streams obtained are listed in table 1.

TABLE 1

| | water | MOP'S | HA | MPG | DPGME | HBC | mass flow [kg/h] |
|---|---|---|---|---|---|---|---|
| feed [wt.-%] | 97.45 | 0.05 | 0.09 | 2.04 | 0.32 | 0.05 | 1000 |
| bottoms C1 [wt.-%] | 96.78 | 0.04 | 0.10 | 2.65 | 0.39 | 0.04 | 767 |
| top C1 [wt.-%] | 99.64 | 0.08 | 0.06 | 0.03 | 0.08 | 0.09 | 233 |
| bottoms C2 [wt.-%] | 95.35 | 0.03 | 0.11 | 3.91 | 0.53 | 0.06 | 516 |
| top C2 [wt.-%] | 99.74 | 0.06 | 0.07 | 0.03 | 0.10 | 0.00 | 250 |
| bottoms C3 [wt.-%] | 91.19 | 0.02 | 0.14 | 7.62 | 0.91 | 0.12 | 264 |
| top C3 [wt.-%] | 99.72 | 0.04 | 0.08 | 0.03 | 0.13 | 0.00 | 252 |
| bottoms C4 [wt.-%] | 8.51 | 0.00 | 0.13 | 82.64 | 7.33 | 1.30 | 24 |
| top C4 [wt.-%] | 99.57 | 0.02 | 0.14 | 0.01 | 0.26 | 0.00 | 227 |
| RO feed [wt.-%] | 99.67 | 0.05 | 0.09 | 0.03 | 0.14 | 0.02 | 976 |
| RO retentate [wt.-%] | 91.24 | 1.38 | 1.94 | 0.73 | 4.07 | 0.64 | 32 |
| RO permeate [wt.-%] | 99.96 | 0.00 | 0.03 | 0.00 | 0.01 | 0.00 | 944 |

Example 2 (Comparative)

Distillation Without Reverse Osmosis

From a storage tank, 1000 kg/h of a waste stream from a process for preparing propylene oxide with a composition according to example 1 is subjected to distillation in four columns which are thermally coupled to obtain top streams of the four columns with a water content of about 99.9 wt.-%.

The columns are coupled in a way, that the first column is heated with steam and each of the following columns is heated with the vapors of the column before.

The columns are operated at the following pressures and reflux ratios:

| | | |
|---|---|---|
| Column 1 (diameter 0.3 m, 25 m high): | 3.0 bar | RR = 0.7 |
| Column 2 (diameter 0.3 m, 25 m high): | 2.2 bar | RR = 0.75 |
| Column 3 (diameter 0.3 m, 25 m high): | 1.5 bar | RR = 0.8 |
| Column 4 (diameter 0.6 m, 18 m high): | 90 mbar | RR = 0.6 |

Columns 1 to 3 use 16 m of sheet metal 250 m$^2$/m$^3$, column 4 uses 10 m of mesh packing 500 m$^2$/m$^3$.

For the above stream of 1 t/h, 256 KW steam are needed for the distillation.

The energy costs (steam and el. energy) for the process according to the invention are about 20% lower combined with an investment which is about 10% lower than for the process according to the state of the art.

The streams obtained are listed in table 2.

TABLE 2

| | water | MOP'S | HA | MPG | DPGME | HBC | mass flow [kg/h] |
|---|---|---|---|---|---|---|---|
| feed [wt.-%] | 97.45 | 0.05 | 0.09 | 2.04 | 0.32 | 0.05 | 1000 |
| bottoms C1 [wt.-%] | 96.73 | 0.03 | 0.11 | 2.67 | 0.42 | 0.04 | 764 |
| top C1 [wt.-%] | 99.87 | 0.11 | 0.01 | 0.00 | 0.00 | 0.00 | 236 |
| bottoms C2 [wt.-%] | 95.31 | 0.01 | 0.16 | 3.85 | 0.60 | 0.06 | 529 |
| top C2 [wt.-%] | 99.93 | 0.06 | 0.01 | 0.00 | 0.00 | 0.00 | 235 |
| bottoms C3 [wt.-%] | 91.69 | 0.01 | 0.27 | 6.85 | 1.07 | 0.11 | 298 |
| top C3 [wt.-%] | 99.96 | 0.03 | 0.01 | 0.00 | 0.00 | 0.00 | 231 |
| bottoms C4 [wt.-%] | 2.00 | 0.00 | 1.78 | 82.03 | 12.83 | 1.27 | 25 |
| top C4 [wt.-%] | 99.86 | 0.01 | 0.13 | 0.00 | 0.00 | 0.00 | 272 |
| waste stream total [wt.-%] | 99.90 | 0.05 | 0.05 | 0.00 | 0.00 | 0.00 | 975 |

We claim:

1. A process for separating at least one propylene glycol from a mixture (M) comprising water and said propylene glycol, said process comprising
   (I) evaporating the mixture in at least two evaporation and/or distillation stages at decreasing operating pressures of the evaporators and/or distillation columns obtaining mixture (M') comprising 80 to 99.9 wt.-% of water and 2.5 to 15 wt.-% of propylene glycol and mixture (M") comprising 90 to 99.99 wt.-% of water and 0.01 to 0.5 wt.-% of propylene glycol,
   wherein mixture (M") is further separated into mixture (M-Ia) comprising at least 90 wt.-% of water and mixture (M-Ib) comprising less than 95 wt.-% of water by subjecting mixture (M") to reverse osmosis; and
   (II) separating the mixture (M') obtained in (I) in at least one further distillation step, obtaining a mixture (M-I) comprising at least 70 wt.-% of water and a mixture (M-II) comprising less than 30 wt.-% of water.

2. The process of claim 1, wherein the process additionally comprises the step
   (III) separating the at least one propylene glycol from the mixture (M-II) in at least one further distillation step.

3. The process of claim 2, wherein mixture (M-Ib) and mixture (M-II) are combined prior to step (III).

4. The process of claim 1, wherein mixture (M-I) is further separated into mixture (M-Ia) comprising at least 90 wt.-% of water and mixture (M-Ib) comprising less than 95 wt.-% of water by subjecting mixture (M-I) to reverse osmosis.

5. The process of claim 1, wherein mixture (M") and mixture (M-I) are combined and further separated, by subjecting to reverse osmosis, into mixture (M-Ia) comprising at least 90 wt.-% of water and mixture (M-Ib) comprising less than 95 wt.-% of water.

6. The process of claim 1, wherein in step (I) three evaporation stages (E1) to (E3) or three distillation stages (D1) to (D3) are carried out.

7. The process of claim 6, wherein the three evaporation stages according to step (I) are carried out at decreasing operating pressures in the ranges
   (E1) 1.5 to 5.5 bar at a temperature of 111 to 155° C.,
   (E2) 1.3 to 5.0 bar at a temperature of 107 to 152° C.,
   (E3) 0.7 to 4.0 bar at a temperature of 90 to 144° C.

8. The process of claim 1, wherein the mixture (M) comprises 0.01 to 25 wt.-% propylene glycol.

9. The process of claim 1, wherein the mixture (M) is obtained as a by-product in a process for the epoxidation of propene.

10. The process of claim 1, wherein the mixture (M) is obtained as a by-product in a process for the epoxidation of propylene comprising the stage
    (a) reacting propylene with a hydroperoxide in the presence of at least one solvent and at least one catalyst to obtain a mixture (M-a) comprising propylene oxide.

11. The process of claim 10, wherein in stage (a) the hydroperoxide is hydrogen peroxide.

12. The process of claim 10, wherein in stage (a) the catalyst is at least one titanium zeolite catalyst and the solvent is methanol.

* * * * *